United States Patent [19]

Laval et al.

[11] Patent Number: 4,837,188

[45] Date of Patent: Jun. 6, 1989

[54] CATALYTIC SYSTEMS HAVING EXTENDED DURATION AND CONSERVATION FOR THE METATHESIS OF OLEFINS

[75] Inventors: Jean-Paul Laval, Roquette; Michel Leconte, Villeurbanne; Jean Ollivier, Arudy; Emile Perez, Coulommiers; Francoise Quignard, Villeurbanne; Isabelle Rico, Ramonville Saint Agne, all of France

[73] Assignee: Societe Nationale Elf Aquitaine, France

[21] Appl. No.: 169,736

[22] Filed: Mar. 18, 1988

[30] Foreign Application Priority Data

Mar. 20, 1987 [FR] France ................................ 87 03879

[51] Int. Cl.$^4$ .......................... C08F 4/62; B01J 31/12; B01J 31/14
[52] U.S. Cl. .................................... 502/107; 502/102; 502/117; 260/405.5; 526/144; 585/643; 585/646
[58] Field of Search ........................ 502/102, 107, 117

[56] References Cited

U.S. PATENT DOCUMENTS 4,137,390  1/1979  Ofstead ............................. 502/117 X
4,239,874 12/1980  Ofstead et al. ................... 502/117 X
4,639,429  1/1987  Basset et al. ......................... 502/117

*Primary Examiner*—Patrick P. Garvin
*Attorney, Agent, or Firm*—Ostrolenk, Faber, Gerb & Soffen

[57] ABSTRACT

Improved catalytic systems of long active duration, comprising initially (a) a tungsten compound, (b) an organometallic compound and (c) a partially or totally fluorinated organic compound.

Process of stabilization of these catalytic systems, comprising dissolving (a) in an organic solvent, contacting (b) with (a), agitation and heating at 0° to 100° C. for 0.5 to 60 minutes, then introduction of (c) into the mixture of (a) and (b).

Use of these stabilised catalytic systems for the metathesis of olefins which carry functional groups or do not carry such groups.

16 Claims, No Drawings

CATALYTIC SYSTEMS HAVING EXTENDED DURATION AND CONSERVATION FOR THE METATHESIS OF OLEFINS

The present invention relates to new catalytic systems having a long active duration, a process for stabilisation and/or conservation of their catalytic activity for a period of time after their preparation, as well as use of these catalytic systems for the metathesis of various olefins.

Metathesis, that is disproportionation of olefins, has been the subject of various studies in recent times because of the practical interest which it affords. It comprises the exchange of groups adjacent the double bond, between two molecules of olefin, giving the possibility of producing compounds which are difficult to synthesise by known methods and also the wide industrial interest which results from this mode of reaction. Operation takes place by heterogeneous or homogeneous catalysis, the catalytic systems generally employed being based upon transition metals such as W, Mo or Re. The reaction can be written diagrammatically:

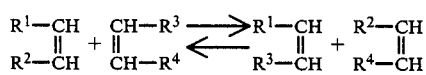  (1)

$R^1$ to $R^4$ designating carbon chains or groups, some of which can be the same, which can carry functions such as for example carboxyls, hydroxyls, amines, amides, nitriles, silyls, halogens, ethers, esters and others.

Homogeneous catalytic systems, often utilised and particularly adapted for the metathesis of olefins which may or may not carry functional groups, are constituted for example by systems which associate tungsten compounds, which have halogen atoms and/or aryloxy ligands, with organometallic compounds, such as organostannic, plumbic, aluminic, lithium or magnesium. Such systems are described particularly in the article by J Otton, Y Colleuille and J Varagnat, in Journal of Molecular Catalysis, 8, 1980, p.313–324, as well as in French Patent Applications Nos. 2 547313 (published Dec. 21, 1984) and 2 565 505 (published December 13, 1985).

Application No. 2 547 513 relates to catalysts of the type:

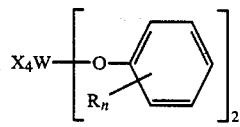

where X is a halogen, R is a hydrocarbon group, an electronegative group or atom and n is an integral number from 1 to 5. Such catalysts associated with compounds of Al or Sn have allowed the disproportionation of various olefins. According to Application No. 2 565 505, the addition of compounds of Pb is preferred in place of compounds of Sn.

While these catalytic systems have a satisfactory activity, they nevertheless have the major disadvantage of only conserving this activity for a relatively short period of time after the combination of their components.

In consequence, their use necessitates their preparation "in situ" at the onset of the catalytic reaction. Their use, particularly in processes on the industrial scale, has a disadvantage for this reason.

The present invention has the object of remedying his disadvantage. In this respect, it provides an important advance. Thus the applicants have found and it is thus one of the objects of this invention that it is possible to conserve catalytic systems for metathesis, based on tungsten compounds, for more than 10 days before they are used, maintaining their activity constant due to the incorporation of a supplementary compound which the prior art has not previously been able to provide.

The present invention is characterised principally by the fact that the supplementary compound is a hydrocarbon which may or may not be saturated, comprising a partially or totally fluorinated hydrocarbon chain.

According to the invention, the catalytic systems comprise initially:

(a) a tungsten compound;
(b) an organometallic compound;
(c) a partially or totally fluorinated organic compound.

The component (c) is more particularly a fluorinated organic compound, saturated or unsaturated, of the general formula

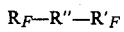

in which $R''$ is a saturated or unsaturated hydrocarbon chain having 0 to 7 carbon atoms, $R_F$ and $R'_F$ are the same or different and are partially or totally fluorinated saturated or unsaturatd carbon chains, preferably totally fluorinated saturated carbon chains, $R_F$ can have 0 to 20 carbon atoms, preferably 0 to 12 atoms, and $R'_F$ 2 to 20 carbon atoms and preferably 2 to 12 atoms.

$R'$ represents preferably a staturated or unsaturated hydrocarbon chain selected from $CH_3-(CH_2)_n$ or $-(CH_2)_{n'}$ n being an integral number from 0 to 6 and n' an integral number from 0 to 5; $CH_2=CH-(CH_2)_m$, m being an integral number from 0 to 3; or $-(CH=CH)-$.

Among the components (c) which can advantageously be used, reference can be made to the following non-limitative list:

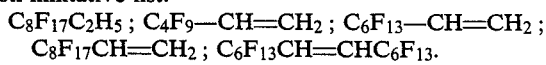

The component (a) has as its general formula:

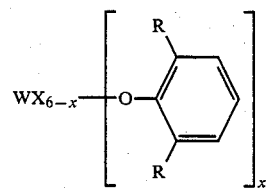

where x is equal to 0 or 2; X is a halogen, preferably chlorine or fluorine; R is a hydrocarbon group or an electronegative group or atom, preferably a $C_1$ to $C_6$ alkyl, a phenyl or a Cl, Br or F atom.

The component (b), an organometallic associated with the component (a), can be one of those where the metal atom is among others Li, Mg, Ti, Al, Sn or Pb, more particularly organoaluminic, stannic or plumbic and preferably compounds of the formula $M(R')_4$ where M is an atom of Sn or of Pb and R' is a $C_1$ to $C_{12}$ alkyl group or a $C_6$ to $C_{18}$ aryl group and more particularly a $C_1$ to $C_5$ alkyl.

According to the invention, the molar ratio of component (c)/component (a) in the initial catalytic system ranges between 0.5/1 and 20/1 and preferably from 0.5/1 to 1/1, while the molar ratio of component (b)/component (a) can be any value found in the known catalysts and more particularly from 1/1 to 4/1, preferably being about 2.

It is appropriate for the catalytic systems of the present invention to be in solution in an organic solvent, which is suitable for homogeneous phase catalysis. Among the very numerous solvents which can be suitable, reference can be made in particular to benzene, toluene, the Freons, $C_6$ to $C_{22}$ saturated hydrocarbons and preferably chlorobenzene.

The process of stabilisation and/or conservation of the activity of the new catalytic systems of the invention comprises dissolving the tungsten compound, that is component (a), in a suitable organic solvent, contacting the organometallic compound (b) with component (a), agitating and heating the reaction mixture which results at a temperature between 0° and 100° C., for 0.5 to 60 minutes, and then introducing an effective quantity of the fluorinated organic product or component (c) and concluding the heating and agitation.

Useful proportions of component (c) introduced correspond to a molar ratio of component (c) to component (a) of 0.5/1 to 20/1. Molar proportions above 20/1, for example 50/1, are employable but are rarely economically justifiable.

According to a preferred embodiment of the process of stabilisation of the invention, the heating time is from 0.5 to 10 minutes when the component (b) is organoplumbic and from 0.5 to 30 minutes in the case of an organostannic compound.

The organic solvent used in the process is more particularly benzene, toluene, the Freons, $C_6$ to $C_{22}$ saturated hydrocarbons and preferably chlorobenzene.

The present invention also has for its purpose the application of the catalytic systems thus stabilised to various types of reaction in the field of metathesis. These reactions can relate both to acrylic olefins which may or may not be functional, more particularly olefinic esters, as well as to cyclic olefins. In these reactions, the molar ratios of olefins/component (a) of the catalytic system can range between 10 and 10000 and preferably between 50 and 2000. These reactions can be carried out at temperatures ranging between 0° C. and 150° C. and more particularly between 25° C. and 85° C.

It will be understood that the catalytic solution according to the invention can be utilised immediately after its preparation. However the merit of the invention which constitutes a very considerable advance with regard to the known art is that this solution can be conserved in this state for more than 10 days. It can thus be used in reactions for the metathesis of olefins without observing any reduction in the catalytic activity, with respect to the activity observed immediately after stabilisation of the catalytic system according to the invention. In fact on the contrary, it appears in a surprising fashion that the high stability of this prepared catalytic system according to the invention allows the conversion, in a given time and for a given quantity of catalyst, of a greater number of molecules of olefin than could be done with the catalytic systems of the prior art. Moreover, it is possible, after reacting one olefin charge, to introduce a new charge into the reaction medium and to convert it, without observing any reduction in the activity of the catalytic system, and this without modifying the reaction medium in any way. After the new charge has itself been converted, a new conversion cycle can be carried out. This type of operation can be repeated several times before observing any appreciable reduction in the activity of the catalytic system of the invention.

The following non-limitative examples have for their sole object the illustration of the various possibilities, the various fields of use and the advantages of the present invention with respect to the prior art.

EXAMPLES 1 to 4

Stabilised catalytic system according to the invention $2.10^{-3}$ mole of tetrabutyltin ($SnBu_4$) is put into contact with $10^{-3}$ mole

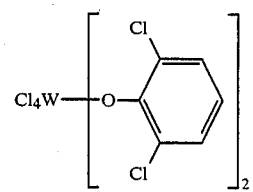

in 10 ml of chlorobenzene at a temperature of 85° C. After 20 minutes of agitation, $10^{-3}$ mole of the fluorinated compound of the formula $C_8F_{17}$—$CH$=$CH_2$ is added. The catalytic solution so obtained is allowed to stand at the ambient temperature.

Use of this catalytic system for the metathesis of cispentene-2

This reaction which gives butene-2 and hexene-3 can be written diagrammatically:

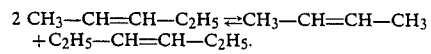

After variable times indicated in Table I, 1 ml of the below-indicated catalytic solution is taken, corresponding to $10^{-4}$ mole of the tungsten compound, $2.10^{-4}$ mole of the tin compound and $10^{-4}$ mole of the fluorinated organic compound, which are introduced into a reactor operating discontinuously, previously purged with argon and maintained at 85° C., with $50.10^{-4}$ mole of cis-pentene-2 in solution in 5 ml of chlorobenzene. The conversion of the cis-pentene-2 is monitored by analysis of the quantity of butene-2 formed.

EXAMPLES 5 AND 6

Comparison with a prior art catalytic system described in French Patent application No. 2 547 513.

In a reactor where operation takes place discontinuously, previously purged with argon, $10^{-4}$ mole of the tungsten compound of examples 1 to 4 is introduced. Then, 5 ml of chlorobenzene serving as a solvent are added. To the solution thus formed, $2.10^{-4}$ mole of tetrabutyltin is added. The reaction mixture is agitated and heated at 85° C. for 20 minutes. In the case of example 5, then $50.10^{-4}$ mole of cis-pentene-2 is introduced and this is followed by the metathesis reaction at 85° C., as in examples 1 to 4, with analysis of the quantity of butene-2 formed. In the case of example 6, the cis-pentene-2 is added 18 hours after preparation of the catalytic solution.

The results of examples 1 to 6, summarised in Table I, show that the catalytic systems of examples 1 to 4 according to the invention allow the attainment of equilibrium of the metathesis reaction of cis-pentene-2 even when the time elapsed between stabilisation of the catalytic system and utilisation of the latter is 10 days. In contrast, the catalytic system of the prior art (examples 5 and 6) does not allow equilibrium of the methathesis reaction to be attained unless it is used immediately after its preparation.

TABLE I

| Examples | Catalytic Systems | t (h)* | $t_r$ (mn)** | Yield of butene*** (mole %) |
|---|---|---|---|---|
| 1 | 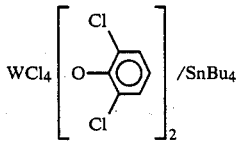 $C_8F_{17}$—CH=CH$_2$ | 18 h | 45 mn | 23% |
| 2 | 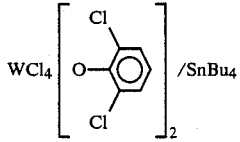 $C_8F_{17}$—CH=CH$_2$ | 93 h | 60 mn | 24% |
| 3 | 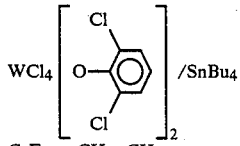 $C_8F_{17}$—CH=CH$_2$ | 160 h | 60 mn | 24% |
| 4 | 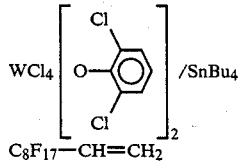 $C_8F_{17}$—CH=CH$_2$ | 240 h | 60 mn | 24% |
| 5 | 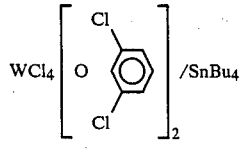 | 0 | 90 mn | 23% |
| 6 | 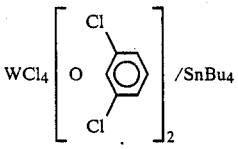 | 18 h | 90 mn | 5% |

*t: time elapsed between stabilisation of the catalytic system and its use in the metathesis of cis-pentene-2.
**$t_r$: duration of the reaction of cis-pentene-2 in the presence of the catalytic system. These results can also be compared with those of Example 42.
***It is known that when the thermodynamic equilibrium of the metathesis is attained, the initial pentene-2 is converted to 25% into butene-2, 25% into hexene-3 and 50% into pentene-2.

EXAMPLES 7 to 9

These examples describe the metathesis of cis-pentene-2 with stabilised catalytic systems as indicated in examples 1 to 4 according to the invention, in which, for each of examples 7 to 9, the fluorinated organic stabilising component (c) is different for the same component (a) and the same component (b). The tests consist in monitoring the metathesis of cis-pentene-2 as indicated in examples 1 to 6. Stabilisation of the catalytic solution is carried out at any point according to the procedure described in examples 1 to 4, in particular the same molar quantity of the organic fluorinated compound is used as the quantity of tungsten compound. The different fluorinated organic compounds utilised are listed in Table II, in the component (c) column. In examples 7 to 9, the various catalytic solutions have all been utilised 18 hours after their preparation, the temperature of the metathesis reaction being 85° C.

The results obtained are summarised in Table II, where the same abbreviations are used as those in Table for examples 1 to 6. These results show that a stabilised catalytic system according to the invention can have several types of fluorinated organic compounds. The new catalytic system conserves the same activity with stabilisers (component (c)) where the length of the fluorinated carbon chain is different (examples 1 and 8), the hydrocarbon part being saturated or unsaturated (examples 1 and 7). The use of internally fluorinated and symmetrical olefins as stabilisers leads to a conversion of pentene-2 comparable to the conversion obtained by means of a catalytic system having a terminally fluorinated olefin (examples 1 and 9).

TABLE II

| | Catalytic Systems | | | | Yield |
|---|---|---|---|---|---|
| Examples | Component (a) | Component (b) | Component (c) | $t_r$ (mn) | (mole %) |
| 1 | 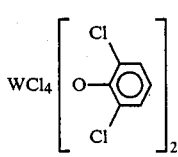 | SnBu$_4$ | $C_8F_{17}$—CH=CH$_2$ | 45 | 23% |

TABLE II-continued

| Examples | Catalytic Systems Component (a) | Component (b) | Component (c) | $t_r$ (mn) | Yield (mole %) |
|---|---|---|---|---|---|
| 7 | WCl$_4$[O-C$_6$H$_3$Cl$_2$]$_2$ | SnBu$_4$ | C$_8$F$_{17}$—CH$_2$—CH$_3$ | 90 | 24% |
| 8 | WCl$_4$[O-C$_6$H$_3$Cl$_2$]$_2$ | SnBu$_4$ | C$_4$F$_9$—CH=CH$_2$ | 90 | 23% |
| 9 | WCl$_4$[O-C$_6$H$_3$Cl$_2$]$_2$ | SnBu$_4$ | C$_8$F$_{17}$—CH=CH—C$_8$F$_{17}$ | 90 | 18% |

EXAMPLES 10 to 13

Catalytic systems according to the invention comprising the same components are stabilized according to examples 1 to 4, but differ however one from the other by variation in the molar ratio of component (c)/component (a), while the molar ratio of component (b)/component (a) remains equal to about 2. These four catalytic systems are applied to the metathesis of cis-pentene-2 at 85° C., 18 hours after their stabilisation. The results indicated in Table III (same abbreviations as in Table I) show that the fluorinated organic product can be utilised advantageously as a stabiliser in a wide range of initial molar ratios of component (c)/component (a) (ranging between 0.5 and 20) which imparts considerable flexibility to their use.

EXAMPLES 14 to 18

The catalytic system of examples 1 to 4 is applied to the metathesis of cis-pentene-2 at different temperatures, in examples 14 to 16. By way of comparison, examples 17 and 18 have been carried out where this metathesis, operated under similar operational conditions, is carried out with the catalytic system of examples 5 to 6 of the prior art. The results of these tests are summarised in Table IV (same abbreviations as in Table I). It is to be noted that the catalytic system of the invention is as active at 25% as at 85%, irrespective of the duration of conservation of the catalytic system between its stabilisation and its use (examples 14 to 16 and 3). Moreover, a clear improvement in the yield of butene at the ambient temperature (25° C.) is noted, with respect to the prior art catalyst (examples 17 to 18).

TABLE III

| Examples | Catalytic System Initial components (a) + (b) + (c) | Initial molar ratios of components (c)/(a) | $t_r$ (mn) | Yield of butene % molar |
|---|---|---|---|---|
| 10 | WCl$_4$[O-C$_6$H$_3$Cl$_2$]$_2$ | 0.5 | 20 | 21 |
| 11 | + SnBu$_4$ + | 1 | 45 | 23 |
| 12 | C$_8$F$_{17}$—CH=CH$_2$ | 5 | 45 | 24 |
| 13 |  | 20 | 45 | 20 |
|  |  | 50 | 45 | 2 |

TABLE IV

| Examples | Catalytic Systems | Temperature of catalytic reaction | t (h) | tr$_{(mn)}$ | Yield of butene (mole %) |
|---|---|---|---|---|---|
| 14 | WCl$_4$[O—C$_6$H$_3$Cl$_2$]$_2$ /SnBu$_4$/ <br> C$_8$F$_{17}$CH=CH$_2$ of examples 1 to 4. | 25° C. | 1 h | 60 | 22% |
| 15 | WCl$_4$[O—C$_6$H$_3$Cl$_2$]$_2$ /SnBu$_4$/ <br> C$_8$F$_{17}$CH=CH$_2$ of examples 1 to 4. | 25° C. | 160 h | 90 | 24% |
| 16 | WCl$_4$[O—C$_6$H$_3$Cl$_2$]$_2$ /SnBu$_4$/ <br> C$_8$F$_{17}$CH=CH$_2$ of examples 1 to 4. | 65° C. | 160 h | 60 | 24% |
| 3 | WCl$_4$[O—C$_6$H$_3$Cl$_2$]$_2$ /SnBu$_4$/ <br> C$_8$F$_{17}$CH=CH$_2$ of examples 1 to 4. | 85° C. | 160 h | 60 | 24% |
| 17 | WCl$_4$[O—C$_6$H$_3$Cl$_2$]$_2$ /SnBu$_4$ <br> of examples 5-6 | 25° C. | 1 h | 60 | 4% |
| 18 | WCl$_4$[O—C$_6$H$_3$Cl$_2$]$_2$ /SnBu$_4$ <br> of examples 5-6 | 25° C. | 160 h | 90 | 0% |

EXAMPLE 19 to 23

The stabilised catalytic system according to examples 1 to 4 is applied to the metathesis of cis-pentene-2 at 25° C. at variable times following its stabilisation, using a molar ratio of cis-pentene-2/component (a) of 100 or 1000. The results are summarised in Table V (same abbreviations as in Table I). Table V also shows example 15 (molar ratio olefin/component (a) equal to 50). By way of comparison (examples 22 to 23), a catalytic system according to French Patent Application Number 2 346 047 has been used, which proposes to add a compound (published Oct. 28, 1979) containing at least one ether function to a catalytic system based on tungsten complexes. The catalytic solution has been prepared as indicated in this publication, then used at variable times following its preparation and at different temperatures. The molar ratios of cis-pentene-2/tungsten component are 1000.

In examples 15 and 19 to 23, the components (a) and (b) of the catalyst system are respectively:

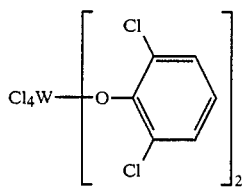

and tetrabutyltin SnBu$_4$.

The molar ratio of components (a)/(b)/(c) is 1/2/1. The component (c) is identified in Table V for each of the examples.

Results will be seen in Table V showing that, even at 25° C. and irrespective of the time elapsed between stabilisation of the catalytic system according to the invention and its use, the activity of this system remains identical for the three molar ratios of olefin/component (a) of 50, 100 and 1000 (examples 15, 19 to 21). However, with the catalytic system of the prior art, stabilised with ether (examples 22 to 23), it will be noted that its activity reduces for the relatively high molar ratios of olefin/component (a), particularly 1000. Even by elevating the temperature of the metathesis reaction from 25° to 65° C., the yield in butene remains practically unchanged (example 23).

These comparative results show that the catalytic systems of the invention are considerably more active than those of the prior art represented by French Patent Application No. 2 346 047.

TABLE V

| Example | Stabilisers | t(h) | Molar ratios olefin/ component (a) | T(°C.) | tr$_{(mn)}$ | Yield of butene mole % |
|---|---|---|---|---|---|---|
| 15 | C$_8$F$_{17}$CH=CH$_2$ | 160 | 50 | 25 | 90 | 24% |
| 19 | idem | 20 | 1000 | 25 | 90 | 24% |
| 20 | idem | 160 | 1000 | 25 | 90 | 24% |
| 21 | idem | 240 | 100 | 25 | 90 | 24% |
| 22 | (C$_2$H$_5$)$_2$O | 18 | 1000 | 25 | 90 | 9% |
| 23 | (C$_2$H$_5$)$_2$O | 160 | 1000 | 65 | 90 | 10% |

EXAMPLES 24 to 26

The catalytic system of example 1 is applied to the metathesis at 25° C. of cis-pentene-2 utilised a molar ratio of cis-pentene-2/tungsten compound (a) equal to 100. After one hour of reaction, a new charge of olefin identical to the first is introduced into the reaction medium. After a further hour, the result of the overall reaction is analysed, that is the first and the second charges cumulatively, and a new operative cycle is effected.

By way of comparison, two catalytic solutions are prepared according to the prior art (examples 25 and 26) containing the same components (a) and (b) and in the same molar proportions as in example 24, except that in example 25 there is no component (c), while in example 26 the component (c) is ether. The catalytic solutions of examples 25 and 26 are then subjected to the same operative conditions for metathesis of cis-pentene-2 as in example 24.

The results, summarised in Table VI (same abbreviations as in Table I) show that only the catalytic solution stabilised by means of the fluorinated organic compound according to the invention (example 24) allows thermodynamic equilibrium of the reaction to be attained with each charge of olefin, without there being any reduction in the catalytic activity.

TABLE VI

| Examples | Stabilisers | t (h) | Molar ratio: cis-pentene-2 / component (a) | t$_r$(mn) | Yield of butene (mole %) total |
|---|---|---|---|---|---|
| 24 | C$_8$F$_{17}$CH=CH$_2$ | 72 | 100 | 60 | 22% |
|  |  |  | +100 | 60 | 22% |
|  |  |  | +100 | 60 | 23% |
|  |  |  | +100 | 60 | 23% |
|  |  |  | +100 | 60 | 23% |
| 25 | none | 0.3 | 100 | 60 | 4% |
|  |  |  | +100 | 60 | 6% |
|  |  |  | +100 | 60 | 10% |
| 26 | (C$_2$H$_5$)$_2$O | 0.3 | 100 | 60 | 22% |
|  |  |  | +100 | 60 | 16% |
|  |  |  | +100 | 60 | 12% |

EXAMPLES 27 to 32

Different stabilised catalytic systems are used as indicated in example 1, containing a molar ratio of components (a)/(b)/(c) equal to 1/2/1 for examples 28, 30 and 32. The metathesis of cis-pentene-2 is carried out at 85° C. with a molar ratio of cis-pentene-2/component (a) of 50.

By way of comparison, catalytic solutions of the prior art have been used (examples 27, 29 and 31) containing the same components (a) and (b), in the same molar ratios as for the catalytic systems of the invention (examples 28, 30 and 32), but without component (c) (fluorinated organic).

The results of the metathesis are summarised in Table VII (same abbreviations as in Table I). They show that the conversion of cis-pentene-2 to butene-2 is higher when the reaction is carried out by means of the catalytic solutions of the invention, irrespective of the nature of the components (a) and (b).

TABLE VII

| Examples | Tungsten compound (a) | Component (b) | Component (c) | t(h) | t_r(mn) | Yield of butene (mole %) |
|---|---|---|---|---|---|---|
| 27 | [WCl4(O-C6H3Cl2)]2 | Sn(CH3)4 | none | 18 | 60 | 15% |
| 28 | " | " | C8F17CH=CH2 | 18 | 60 | 25% |
| 29 | [WCl4(O-C6H3(C6H5)2)]2 | Pb(C4H9)4 | none | 18 | 30 | 7% |
| 30 | " | " | C8F17CH=CH2 | 18 | 30 | 21% |
| 31 | WCl4 | Sn(CH3)4 | none | 68 | 90 | 0% |
| 32 | " | " | C8F17CH=CH2 | 68 | 90 | 20% |

EXAMPLES 33 to 35

The metathesis of an olefin carrying functional groups (ethyl oleate) with a catalytic system according to the invention is carried out, which is compared with a catalytic system of the prior art.

The tests consist in maintaining ethyl oleate at 85° C. in the presence of a catalytic system according to the invention (example 33) or prepared according to the prior art (examples 34 and 35) and determining the percent of ocadecene-9 formed following the reaction:

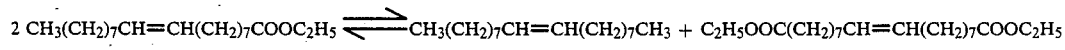

2 CH3(CH2)7CH=CH(CH2)7COOC2H5 ⇌ CH3(CH2)7CH=CH(CH2)7CH3 + C2H5OOC(CH2)7CH=CH(CH2)7COOC2H5 which provides at the same time ethyl hexadecene-8-di-1,16-carboxylate.

In examples 34 and 35, the metathesis of ethyl oleate is carried out with the catalytic system

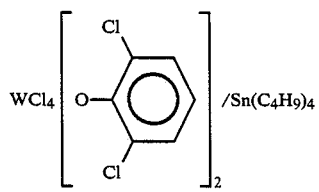
/Sn(C4H9)4 of the prior art under conditions analogous to those used in the case of the metathesis of cis-pentene-2 and described in the foregoing examples 5 and 6. This catalytic solution is utilised either immediately (example 34) or 18 hours (example 35) after its preparation. In example 33, the metathesis of ethyl oleate is carried out utilising the catalytic system

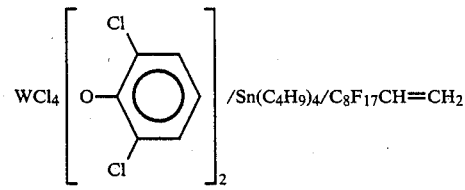

prepared according to the invention and in conditions analogous to those used in the case of the metathesis of cis-pentene-2 and described in examples 1 to 4. The catalytic solution was utilised 18 hours after its preparation.

In the three examples 33 to 35, the molar ratio of ethyl oleate/tungsten compound is 50 and the molar ratio of component (b)/component (a) is 2. In example 33, the molar ratio of component (c)/component (a) is equal to 1. The reaction of metathesis of ethyl oleate is carried out at 85° C. After reaction for 60 minutes, the liquid phase is analysed to determine the yield of octadecene-9, that is the percent ratio of the number of moles of this compound formed to the number of moles of the oleate used. Table VIII sets out the results obtained (same abbreviations as in Table I).

TABLE VIII

| Examples | Catalytic Systems | t (h) | t_r (mn) | Yield of octadecene-9 (mole %) |
|---|---|---|---|---|
| 34 | [WCl4(O-C6H3Cl2)]2 /SnBu4 | 0 | 60 mn | 13% |

TABLE VIII-continued

| Examples | Catalytic Systems | t (h) | $t_r$ (mn) | Yield of octa-decene-9 (mole %) |
|---|---|---|---|---|
| 35 | " | 18 h | 60 mn | 0% |
| 33 |  WCl$_4$[structure with Cl, O-phenyl, Cl]$_2$/SnBu$_4$/ C$_8$F$_{17}$CH=CH$_2$ | 18 h | 60 mn | 13% |

The results of Table VIII show that a catalytic system of the prior art only effects the metathesis of ethyl oleate if it is utilised immediately after its preparation (examples 34 and 35). By contrast, the catalytic system according to the invention allows the metathesis of ethyl oleate to be carried out even when it is used 18 hours after its preparation.

EXAMPLES 36 to 38

Use of a catalytic system according to the invention for the cross metathesis of olefinic acid esters and olefins.

The reaction studied, which is a route for the synthesis of insect pheromones, is shown diagrammatrically as follows:

$$CH_3(CH_2)_7CH=CH(CH_2)_7COOC_2H_5 + CH_3(CH_2)_3CH=CH(CH_2)_3CH_3$$
$$\text{I} \qquad \text{II}$$

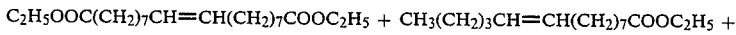
$$C_2H_5OOC(CH_2)_7CH=CH(CH_2)_7COOC_2H_5 + CH_3(CH_2)_3CH=CH(CH_2)_7COOC_2H_5 +$$
$$\text{III} \qquad \text{IV}$$

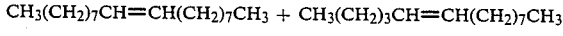
$$CH_3(CH_2)_7CH=CH(CH_2)_7CH_3 + CH_3(CH_2)_3CH=CH(CH_2)_7CH_3$$
$$\text{V} \qquad \text{VI}$$

This reaction between ethyl oleate and decene-5 has been carried out, on the one hand, by employing a catalytic system according to the invention:

WCl$_4$[structure with Cl, O-phenyl, Cl]$_2$/SnBu$_4$/C$_8$F$_{17}$CH=CH$_2$, used 200 hours after its preparation (example 36) and, on the other hand, by employing a catalytic system of the prior art.

WCl$_4$[structure with Cl, O-phenyl, Cl]$_2$/SnBu$_4$), used either immediately (example 37) or 200 hours after its preparation (example 38).

In the three examples, the molar ratio of decene-5/ethyl oleate is equal to 2 and the molar ratio of ethyl oleate/tungsten compound is equal to 50. The other conditions are the same as those used in examples 33 to 35. After 90 minutes of reaction at 85° C., the liquid phase is analysed to determine the rate of conversion of the ethyl oleate (I) and the yield of product (IV) (calculated in molar percent with respect to the initial oleate). The results are given in Table IX (same abbreviations as in Table I).

TABLE IX

| Examples | Catalytic Systems | t (h) | $t_r$ (mn) | Conversion of oleate (mole %) | Yield of IV (mole %) |
|---|---|---|---|---|---|
| 36 | WCl$_4$[structure with Cl, O-phenyl, Cl]$_2$/SnBu$_4$  C$_8$F$_{17}$CH=CH$_2$ | 200 h | 90 mn | 85% | 50% |

TABLE IX-continued

| Examples | Catalytic Systems | t (h) | $t_r$ (mn) | Conversion of oleate (mole %) | Yield of IV (mole %) |
|---|---|---|---|---|---|
| 37 | 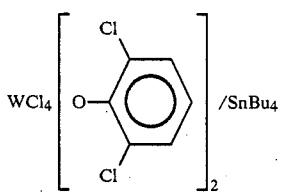 | 0 | 90 mn | 56% | 50% |
| 38 | " | 200 h | 90 mn | 0% | 0% |

These results show that, contrary to the catalytic systems of the prior art, the catalytic system according to the invention, more than 8 days after its preparation, makes it possible to carry out the reaction of cross metathesis between an olefinic acid ester and an olefin.

EXAMPLES 39 to 41

Use of a catalytic system according to the invention for the metathesis of a cyclic olefin The tests consist in carrying out the polymerisation by metathesis of dicyclopentadiene, on the one hand with a catalytic system according to the invention

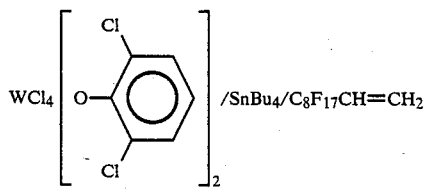

used 200 hours after its preparation (example 39) or, on the other hand, with a catalytic system according to the prior art

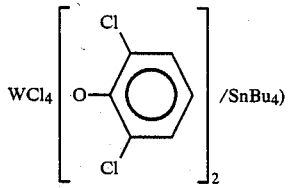

used immediately (example 40) or 200 hours after its preparation (example 41).

In the three examples 39 to 41, the molar ratios of dicyclopentadiene/tungsten compound are equal to 500 and the molar ratios of component (b)/component (a) are equal to 2. In example 39, the molar ratio of component (c)/component (a) is equal to 1. The methods of preparation and use of the catalytic systems of the prior art and of the invention are the same as those described in the foregoing examples 1 to 6.

The polymerisation reaction is carried out at 85° C. After an hour of reaction, the yield of polydicyclopentadiene is measured. The results obtained are summarised in Table X (same abbreviations as in Table I).

The results show in a surprising fashion that a catalytic system according to the invention, more than 8 days after its preparation, allows the polymerisation by metathesis of a cyclic olefin to be carried out. Under the same conditions, a catalytic system of the prior art shows no activity.

TABLE X

| Ex. | Catalytic Systems | t (h) | $t_r$ (mn) | Yield of poly-dicyclopentadiene (%) |
|---|---|---|---|---|
| 39 | $WCl_4[O\text{-}C_6H_3Cl_2]_2/SnBu_4$ $C_8F_{17}CH=CH_2$ | 180 h | 60 mn | 100% |
| 40 | $WCl_4[O\text{-}C_6H_3Cl_2]_2/SnBu_4$ | 0 | 60 mn | 100% |
| 41 | " | 180 h | 60 mn | 0% |

The action of the fluorinated compounds shown in the foregoing examples is especially surprising, because other organic halides do not enable stabilisation of tungsten catalysts for metathesis. In fact, if Cl, Br, or I halides as described in U.S. Pat. No. 4 262 156 can serve as initiators, in the presence of an organo-tin compound, they do not allow conservation of the catalyst for several hours before its use. According to the U.S. patent cited, a halide effective as an initiator would be carbon tetrachloride, $CCl_4$, for example (col. 10, Table I, tests numbers 10 to 13 and 28 to 30). This has been tried within the scope of the present invention, in the following example 42, and it has been confirmed that this does not allow the catalyst to be conserved for several hours with a metathesis reaction.

EXAMPLE 42

Cis-pentene-2 is subjected to metathesis exactly as in example 6 given above and summarised in Table I, except that 20 minutes after preparation of the catalyst at 85° C., $10^{-4}$ mole of $CCl_4$ is added. The catalyst is then allowed to stand at ambient temperature for 18 hours. Utilised after this time, the catalyst only gives a yield of 0.5% of butene-2, after 90 minutes of reaction at 85° C., as against 23% for example 1.

We claim:
1. A catalytic system for the metathesis of olefins, which comprises:
(a) a tungsten halide of the formula

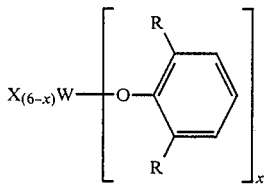

where x is 0 or 2, X is a halogen atom, and R is a hydrocarbyl or an electronegative atom or group;
(b) an organometallic compound of Li, Mg, Ti, Al, Sn or Pb, and
(c) a fluorinated organic compound having the structure of $R_F—R''—R'_F$ in which R'' is a saturated or unsaturated hydrocarbon chain having 0 to 7 carbon atoms, while $R_F$ and $R'_F$ are hydrocarbon chains partially or totally fluorinated, $R_F$ having 0 to 20 carbon atoms and $R'_F$ 2 to 20 carbon atoms.

2. The catalytic system according to claim 1, wherein R'' is a hydrocarbon chain selected from the group consisting of $CH_3(CH_2)_n—$, $—(CH_2)_{n'}—$, $CH_2=CH(CH_2)_m—$ and $—CH=CH—$, n being an integer of 0 to 6, n' an integer of 0 to 5 and m an integer of 0 to 3, while $R_F$ and $R'_F$ are saturated hydrocarbon chains totally fluorinated, $R_F$ having 0 to 12 carbon atoms and $R'_F$ 2 to 12 carbon atoms.

3. The catalytic system according to claim 1, in which component (a) is

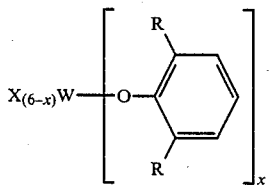

where x=0 or 2, X is Cl or F, and R is a lower alkyl, Cl, F or Br.

4. The catalytic system according to claim 1, wherein component (b) is an organo compound of Al, Ti, Li, or Mg.

5. The catalytic system according to claim 1, wherein component (b) is an organo metallic compound $M(R')_4$ M being a Sn or Pb atom and R' an alkyl having 1 to 12 carbon atoms or an aryl having 6 to 12 carbon atoms.

6. The catalytic system of claim 1, which contains a solvent selected from the group consisting of benzene, toluene, saturated $C_6$ to $C_{22}$ hydrocarbons, fluorocarbons and chlorobenzenes.

7. The catalytic system of claim 1, wherein the molar ratio of component (c) to component (a) is initially 0.5/1 to 20/1.

8. The catalytic system of claim 1, wherein the molar ratio of component (b) to component (a) is comprised between 1 and 4.

9. A method of preparing the catalytic system according to claim 1, which comprises dissolving component (a) in an organic solvent adding component (b) to the solution thus obtained, stirring the solution while heating it to a temperature of 0° to 100° C. during 0.5 to 60 minutes, then introducing thereinto 0.5 to 20 moles of component (c) per mole of component (a) and ceasing heating and stirring.

10. The method of claim 9 wherein (c) is $C_4F_9CH=CH_2$, $C_8F_{17}CH_2CH_3$ or $C_8F_{17}CH=CHC_8F_{17}$.

11. The method of claim 9 wherein (c) is $C_8F_{17}CH=CH_2$.

12. The catalytic system according to claim 3, wherein X and R are Cl.

13. The catalytic system according to claim 12, wherein x is 2 and (b) is $SnR'_4$ where R' is alkyl having 1 to 12 carbon atoms.

14. The catalytic system according to claim 13 wherein R' is butyl and the molar ratio of component (c) to component (a) is initially 0.5/1 to 20/1.

15. The catalytic system according to claim 14 wherein (c) is $C_4F_9CH=CH_2$, $C_8F_{17}CH_2CH_3$ or $C_8F_{17}CH=CHC_8F_{17}$.

16. The catalytic system according to claim 14 wherein (c) is $C_8F_{17}CH=CH_2$.

* * * * *